United States Patent
Law et al.

(10) Patent No.: US 6,815,133 B2
(45) Date of Patent: Nov. 9, 2004

(54) SULFONYLDIPHENYLENE BASED CHARGE TRANSPORT COMPOSITIONS

(75) Inventors: Kam W. Law, Woodbury, MN (US); Nusrallah Jubran, St. Paul, MN (US); Zbigniew Tokarski, Woodbury, MN (US)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/382,393

(22) Filed: Mar. 6, 2003

(65) Prior Publication Data

US 2003/0203297 A1 Oct. 30, 2003

Related U.S. Application Data

(60) Provisional application No. 60/372,293, filed on Apr. 12, 2002.

(51) Int. Cl.$^7$ .................. G03G 5/047; C07C 25/124
(52) U.S. Cl. .................. 430/58.45; 430/72; 430/117; 564/251
(58) Field of Search .................. 430/58.35, 58.6, 430/79, 117, 58.45, 72; 548/440; 564/251

(56) References Cited

U.S. PATENT DOCUMENTS

| | | | |
|---|---|---|---|
| 3,932,455 A | 1/1976 | Bilofsky et al. | |
| 3,943,108 A | 3/1976 | Teuscher | |
| 4,072,519 A | 2/1978 | Pearson et al. | |
| 4,297,426 A | 10/1981 | Sakai et al. | |
| 4,322,487 A | 3/1982 | Merrill et al. | |
| 4,426,327 A | 1/1984 | Hashimoto et al. | |
| 4,476,137 A | 10/1984 | Haviv et al. | |
| 4,786,571 A | 11/1988 | Ueda | |
| 4,957,838 A | 9/1990 | Aruga et al. | |
| 5,128,227 A | 7/1992 | Monbaliu et al. | |
| 5,274,116 A | 12/1993 | Martin et al. | |
| 5,932,384 A | 8/1999 | Mitsumori et al. | |
| 6,001,522 A | 12/1999 | Woo et al. | |
| 6,020,096 A | 2/2000 | Fuller et al. | |
| 6,030,734 A | 2/2000 | Mitsumori | |
| 6,066,426 A | 5/2000 | Mott et al. | |
| 6,099,996 A | 8/2000 | Yanus et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,689,523 B2 * | 2/2004 | Law et al. | 430/58.35 |
| 6,696,209 B2 * | 2/2004 | Law et al. | 430/58.35 |
| 2002/0064397 A1 | 5/2002 | Kellie et al. | |
| 2002/0122997 A1 | 9/2002 | Lee et al. | |

FOREIGN PATENT DOCUMENTS

EP     1 202 120 A2     5/2002

* cited by examiner

*Primary Examiner*—John L Goodrow
(74) *Attorney, Agent, or Firm*—Patterson, Thuente, Skaar & Christensen, P.A.

(57) ABSTRACT

This invention relates to a novel organophotoreceptor that includes:

(a) a charge transport composition comprising molecules having the formula

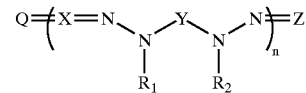

where the average n is between 1 and 1000;

$R_1$ and $R_2$ are, independently, hydrogen, a branched or linear alkyl group (e.g., a $C_1$–$C_{30}$ alkyl group), a branched or linear unsaturated hydrocarbon group, an ether group, a cycloalkyl group (e.g. cyclohexyl group), or an aryl group (e.g., a phenyl or naphthyl group);

X is a bis(fluorene-4-carboxyl)alkane group;

Y is a divalent sulfonyldiphenylene group;

Z is X═O where X is double-bonded to the adjacent N or two hydrogens where each hydrogen is independently single-bonded to the adjacent N; and Q is O or N—N($R_1$)—Y—N($R_2$)—NH$_2$;

(b) a charge generating compound; and (c) an electrically conductive substrate over which said charge transport composition and said charge generating compound are located.

12 Claims, No Drawings

SULFONYLDIPHENYLENE BASED CHARGE TRANSPORT COMPOSITIONS

CROSS REFERENCE TO RELATED APPLICATIONS

The application claims priority to U.S. Provisional Patent Application Ser. No. 60/372,293 filed on Apr. 12, 2002 to Law et al., entitled "Electrophotographic Organophotoreceptors With Novel Polymeric Charge Transport Compounds," incorporated herein by reference.

FIELD OF INVENTION

This invention relates to organophotoreceptors suitable for use in electrophotography and, more specifically, to flexible organophotoreceptors having improved charge transport compositions comprising a bis(9-fluorenone-4-carboxyl)alkane sulfonyldiphenylenebishydrazone group, and in some embodiments a polymer, such as an oligomer, derived from repeating units of bis(9-fluorenone-4-carboxyl)alkane sulfonyldiphenylene-bishydrazone group.

BACKGROUND

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas. A liquid or solid toner is then deposited in either the charged or uncharged areas depending on the properties of the toner to create a toned image on the surface of the photoconductive layer. The resulting toned image can be transferred to a suitable receiving surface such as paper. The imaging process can be repeated many times to complete a single image and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport compound is to accept at least one type of these charge carriers, generally holes, and transport them through the charge transport layer in order to facilitate discharge of a surface charge on the photoconductive element.

SUMMARY OF THE INVENTION

In a first aspect, the invention features an organophotoreceptor that includes:

(a) a charge transport composition comprising molecules having the formula

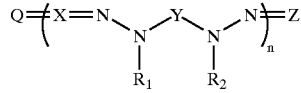

where the average n is between 1 and 1000;

$R_1$ and $R_2$ are, independently, hydrogen, a branched or linear alkyl group (e.g., a $C_1$–$C_{30}$ alkyl group), a branched or linear unsaturated hydrocarbon group, an ether group, a cycloalkyl group (e.g. a cyclohexyl group), or an aryl group (e.g., a phenyl or naphthyl group);

X is a bis(fluorene-4-carboxyl)alkane group;

Y is a divalent sulfonyldiphenylene group;

Z is X═O where X is double-bonded to the adjacent N or two hydrogens where each hydrogen is independently single-bonded to the adjacent N; and Q is O or N—N($R_1$)—Y—N($R_2$)—$NH_2$;

(b) a charge generating compound; and (c) an electrically conductive substrate over which the charge transport composition and the charge generating compound are located.

In a second aspect, the invention features an electrophotographic imaging apparatus that includes (a) a plurality of support rollers; and (b) the above-described organophotoreceptor operably coupled to the support rollers with motion of the support rollers resulting in motion of the organophotoreceptor. The apparatus preferably further includes a liquid or solid toner dispenser.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a liquid or dry toner to create a toned image; and (d) transferring the toned image to a substrate.

In a fourth aspect, the invention features a novel charge transport material having the formula (a) a charge transport composition comprising molecules having the formula

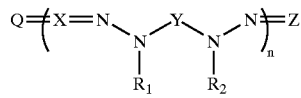

where the average n is between 1 and 1000;

$R_1$ and $R_2$ are, independently, hydrogen, a branched or linear alkyl group (e.g., a $C_1$–$C_{30}$ alkyl group), a branched or linear unsaturated hydrocarbon group, an ether group, a cycloalkyl group (e.g. a cyclohexyl group), or an aryl group (e.g., a phenyl or naphthyl group);

X is a bis(fluorene-4-carboxyl)alkane group;

Y is a divalent sulfonyldiphenylene group;

Z is X═O where X is double-bonded to the adjacent N or two hydrogens where each hydrogen is independently single-bonded to the adjacent N; and Q is O or N—N($R_1$)—Y—N($R_2$)—$NH_2$.

These photoreceptors can be used successfully with liquid toners to produce high quality images. The high quality of the images can be maintained after repeated cycling.

Other features and advantages of the invention will be apparent from the following description of the preferred embodiments thereof, and from the claims.

DETAILED DESCRIPTION

Charge transport compositions with desirable properties can be formed having a sulfonyldiphenylene group bonded with two hydrazone groups with the hydrazones having substitutions with at least one of the hydrazone groups being bonded to a bis(fluorene-4-carbonyl)alkane group. In some embodiments, the charge transport composition is a polymer with the hydrazone groups along the polymer chain being bonded to the difunctional bis(fluorene-4-carbonyl)alkane group. These charge transport compositions have desirable properties with respect to their performance in organophotoreceptors for electrophotography. The organophotoreceptors are particularly useful in laser printers and the like as well as photocopiers, scanners and other electronic devices based on electrophotography. The use of these charge transport compositions is described below in the context of laser printers use, although their application in other devices operating by electrophotography can be generalized from the discussion below.

To produce high quality images, particularly after multiple cycles, it is desirable for the charge transport compositions to form a homogeneous solution with the polymeric binder and remain approximately homogeneously distributed through the organophotoreceptor material during the cycling of the material. In addition, it is desirable to increase the amount of charge that the charge transport compositions can accept (indicated by a parameter known as the acceptance voltage or "$V_{acc}$"), and to reduce retention of that charge upon discharge (indicated by a parameter known as the discharge voltage or "$V_{dis}$").

There are many charge transport compositions available for electrophotography. Examples of charge transport materials are pyrazoline derivatives, fluorene derivatives, oxadiazole derivatives, stilbene derivatives, hydrazone derivatives, carbazole hydrazone derivatives, polyvinyl carbazole, polyvinyl pyrene, or polyacenaphthylene. However, there is a need for other charge transport compositions to meet the various requirements of particular electrophotography applications.

In electrophotography applications, a charge generating compound within an organophotoreceptor absorbs light to form electron-hole pairs. These electron-hole pairs can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compositions described herein are especially effective at transporting charge, and in particular holes from the electron-hole pairs formed by the charge generating compound. In some embodiments, a specific electron transport compound can also be used along with the charge transport composition.

The layer or layers of materials containing the charge generating compound and the charge transport compositions are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport composition can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport composition and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport composition and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toned image is the same as or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toned image, to attract toner to the charged or discharged regions of the organophotoreceptor; and (d) transferring the toned image to a substrate.

The improved charge transport compositions described herein comprise a sulfonyldiphenylene group bonded with two hydrazone groups with the hydrazones having substitutions with at least one of the hydrazone groups being bonded to a bis(fluorene-4-carbonyl)alkane group. In some embodiments, the charge transport composition is a polymer with the hydrazone groups along the polymer chain being bonded to the difunctional bis(fluorene-4-carbonyl)alkane group. Specifically, the improved charge transport compositions comprise molecules have the formula:

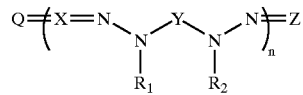

where the average n is between 1 and 1000, such that the polymers, including for example oligomers, have n greater than 1. X is a bis(fluorene-4-carboxyl)alkane group and Y is a divalent sulfonyldiphenylene group.

In describing chemicals by structural formulae and group definitions, certain terms are used in a nomenclature format that is chemically acceptable. The terms groups and moiety have specific meanings. The term group indicates that the generically recited chemical material (e.g., alkyl group, phenyl group, julolidine group, triphenyl amine group, carbazole group, alkylsulfonylphenyl group, etc.) may have any substituent thereon which is consistent with the bond structure of that group. For example, alkyl group includes alkyl materials such as methyl ethyl, propyl iso-octyl, dodecyl and the like, and also includes such substituted alkyls such as chloromethyl, dibromoethyl, 1,3-dicyanopropyl, 1,3,5-trihydroxyhexyl, 1,3,5-trifluorocyclohexyl, 1-methoxydodecyl, phenylpropyl and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, orthocyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical material is not substituted.

Organophotoreceptors

The organophotoreceptor may be, for example, in the form of a plate, a flexible belt, a disk, a rigid drum, or a sheet around a rigid or compliant drum, with flexible belts and rigid drums generally being used in commercial embodiments. The organophotoreceptor may comprise, for example, an electrically conductive substrate and a photoconductive element in the form of one or more layers. The photoconductive element comprises both a charge transport composition and a charge generating compound in a polymeric binder, which may or may not be in the same layer. For example, in some embodiments with a single layer construction, the charge transport composition and the charge generating compound are in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer. In the dual layer embodiments, the charge generation layer generally has a thickness form about 0.5 to about 2 microns, and the charge transport layer has a thickness from about 5 to about 35 microns. In a single layer embodiment, the layer with the charge generating compound and the charge transport composition generally has a thickness from about 7 to about 30 microns.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyethylene terepthalate, polyimide, polysulfone, polyethylene naphthalate, polypropylene, nylon, polyester, polycarbonate, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodide, conductive polymers such as polypyroles and Calgon conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dye or pigment. Examples of suitable charge generating compounds include metal-free phthalocyanines, metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmiumselenide, cadmium sulphide, and mixtures thereof. For some embodiments, the charge generating compound comprises oxytitanium phthalocyanine, hydroxygallium phthalocyanine or a combination thereof.

Generally, a charge generation layer comprises a binder in an amount from about 10 to about 90 weight percent and more preferably in an amount of from about 20 to about 75 weight percent, based on the weight of the charge generation layer. A charge transport layer generally comprises a binder in an amount from about 30 weight percent to about 70 weight percent. A single layer with a charge transport composition and a charge generating compound generally comprises a binder in an amount from about 10 weight percent to about 60 weight percent. A person of ordinary skill in the art will recognize that additional ranges of binder concentrations are contemplated and are within the present disclosure.

The binder generally is capable of dispersing or dissolving the charge transport composition (in the case of the charge transport layer or a single layer construction) and/or the charge generating compound (in the case of the charge generating layer or a single layer construction). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak, poly(phenylglycidyl ether)-co-dicyclopentadiene, copolymers of monomers used in the above-mentioned polymers, and combinations thereof. Preferably, the binder is selected from the group consisting of polycarbonates, polyvinyl butyral, and a combination thereof. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates. Examples of suitable of polyvinyl butyral are BX-1 and BX-5 from Sekisui Chemical Co. Ltd., Japan.

The photoreceptor may optionally have additional layers as well. Such additional layers can be, for example, a sub-layer and overcoat layers such as barrier layers, release layers, and adhesive layers. The release layer forms the uppermost layer of the photoconductor element. The barrier layer may be sandwiched between the release layer and the photoconductive element or used to overcoat the photoconductive element. The barrier layer provides protection from abrasion to the underlayers and protection from the carrier liquid if liquid toners are used. The adhesive layer locates and improves the adhesion between the photoconductive element, the barrier layer and the release layer, or any combination thereof. The sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

Generally, adhesive layers comprise a film forming polymer, such as polyester, polyvinylbutyral, polyvinylpyrolidone, polyurethane, polymethyl methacrylate, poly(hydroxy amino ether) and the like.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be 1–25 microns thick.

The charge transport compositions as described herein, and photoreceptors including these compounds, are suitable for use in an imaging process with either dry or liquid toner development. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 2:1 to 10:1, and in other embodiments, from 4:1 to 8:1. Liquid toners are described further in Published U.S. Patent Applications 2002/0128349, entitled "Liquid Inks COmprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Compositions

In some embodiments, the organophotoreceptors as described herein can comprise an improved charge transport composition with two sulfonylphenylhydrazone groups having the formula

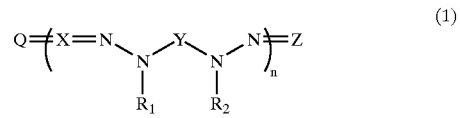

(1)

where the average n is between 1 and 1000;

$R_1$ and $R_2$ are, independently, hydrogen, a branched or linear alkyl group (e.g., a $C_1$–$C_{30}$ alkyl group), a branched or linear unsaturated hydrocarbon group, an ether group, a cycloalkyl group (e.g. a cyclohexyl group), or an aryl group (e.g., a phenyl or naphthyl group);

X is a bis(fluorene-4-carboxyl)alkane group;

Y is a divalent sulfonyldiphenylene group;

Z is either X=O where the bis(fluorene-4-carboxyl) alkane group is double-bonded to the adjacent N, or two hydrogens where each hydrogen is independently single-bonded to the adjacent N; and Q is double bonded O or N—N($R_1$)—Y—N($R_2$)—$NH_2$. When n is greater than 1, the composition generally comprises polymers with a distribution of n values, as is typical with polymers generally. In some embodiments, the average n is between 1 and 20. A person of ordinary skill in the art will recognize that additional ranges of the degree of polymerization, i.e., average n, are contemplated and are within the present disclosure.

The divalent bis(fluorene-4-carboxyl)alkane group of this invention has a chemical structure as shown in Formula (2) where m is between 2 and 30; and $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitrile group, nitro group, an amino group, a cycloalkyl group (e.g. a cyclohexyl group), an aryl group (e.g., a phenyl or naphthyl group), or a part of cyclic or polycyclic ring.

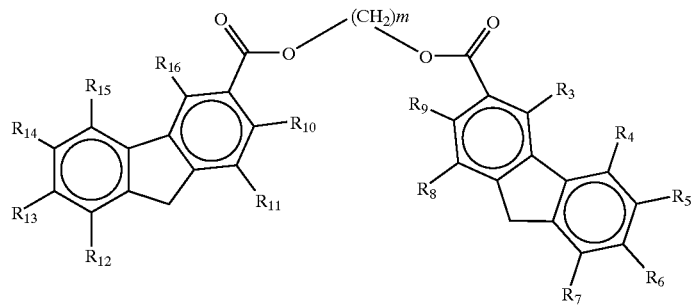

(2)

The divalent sulfonyldiphenylene group of this invention has one of the following chemical structures as shown in Formula (3)–(5) where $R_{17}$, $R_{18}$, $R_{19}$, $R_{20}$, $R_{21}$, $R_{22}$, $R_{23}$, and $R_{24}$ are, independently, hydrogen, a halogen atom, hydroxy group, thiol group, an alkoxy group, a branched or linear alkyl group (e.g., a $C_1$–$C_{20}$ alkyl group), a branched or linear unsaturated hydrocarbon group, an ether group, nitrile group, nitro group, an amino group, a cycloalkyl group (e.g. a cyclohexyl group), an aryl group (e.g., a phenyl or naphthyl group) or a part of cyclic or polycyclic ring.

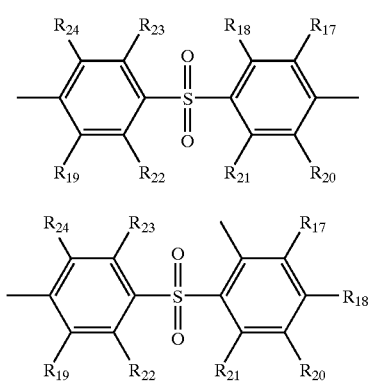

(3)

(4)

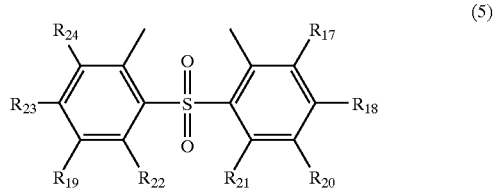

(5)

The N=Z bond in Formula (1) can be either a double bond or two single bonds. When it is a double bond, Z is X=O. When it comprises two single bonds, Z is two hydrogen atoms, each independently single-bonds to the adjacent nitrogen. The charge transport composition may or may not be symmetrical. In addition, the above-described formula for the charge transport composition is intended to cover isomers such as Formula (3) to (5) above.

Non-limiting examples of the charge transport composition of this invention have the following formula where n is between 1 and 1000.

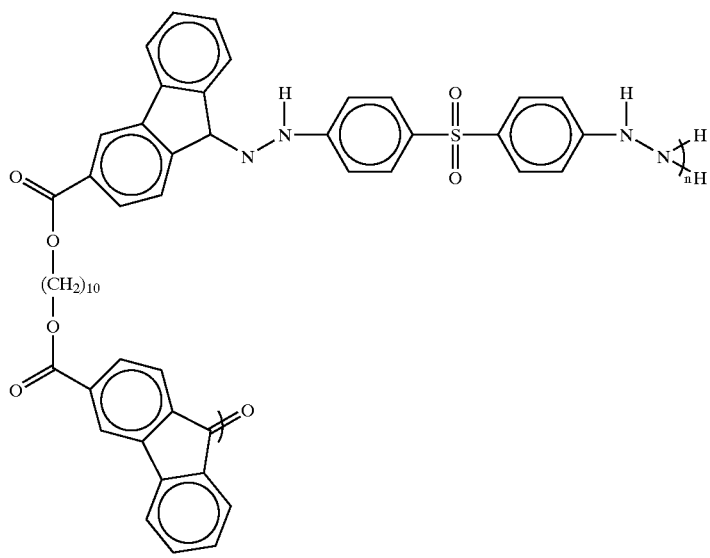

(6)

-continued
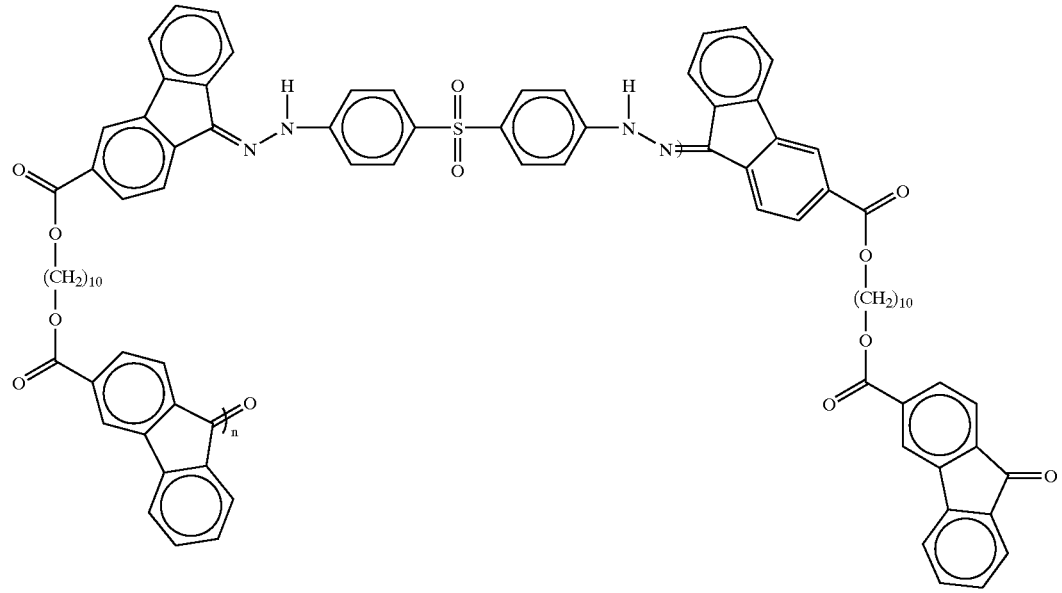
(7)
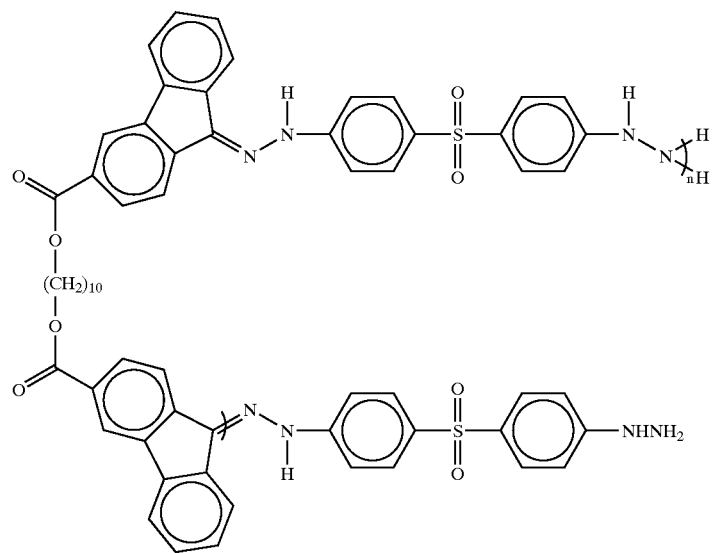
(8)

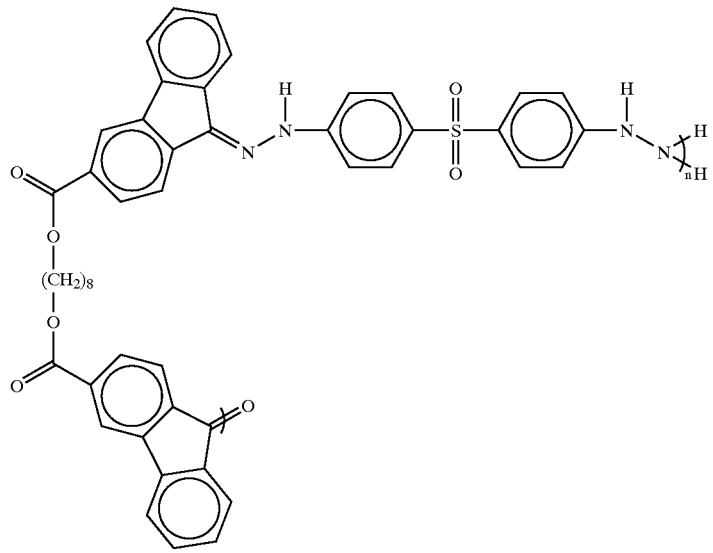
(9)
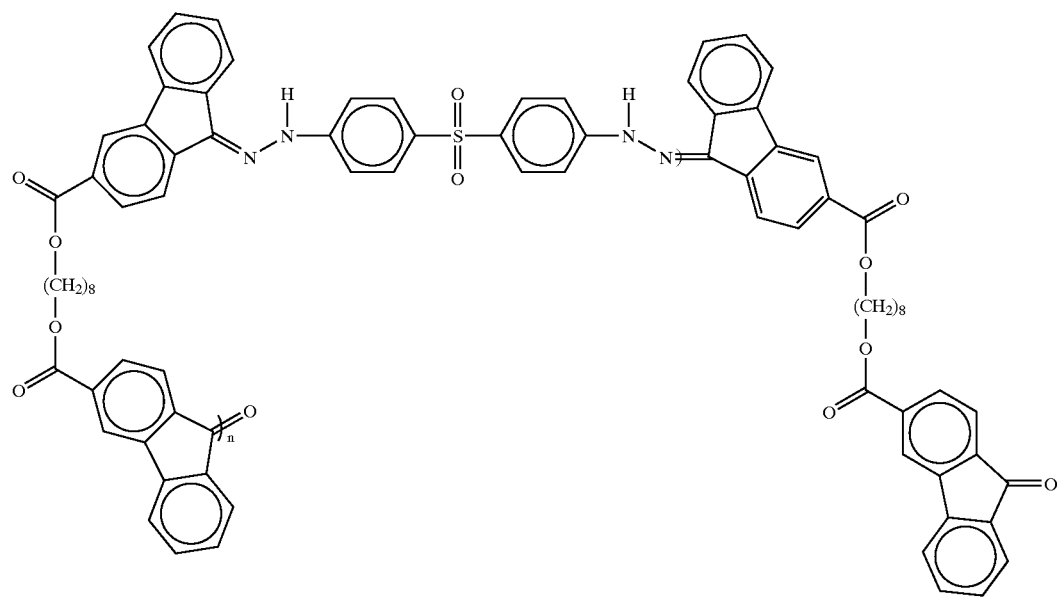
(10)

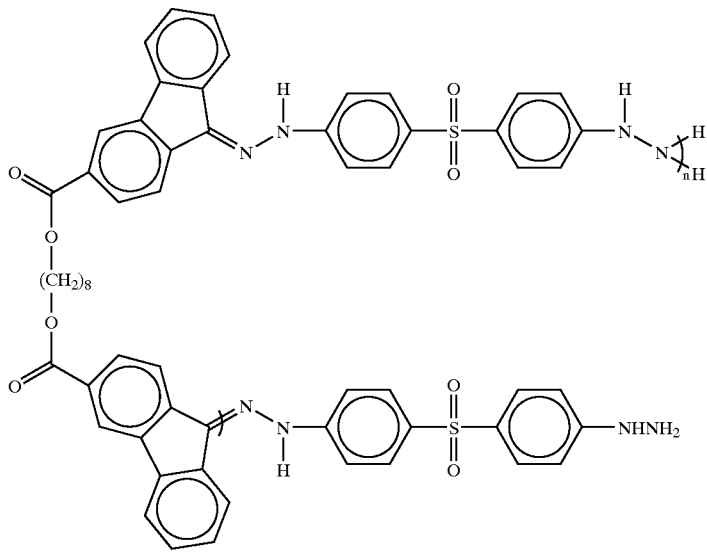
(11)

Synthesis of Charge Transport Compositions

The charge transport compositions generally can be synthesized from a bis(fluorene-4-carbonyl)alkane compound and a (1,1'-(sulfonyldi-4,1-phenylene) bishydrazine compound in an acid catalyzed reaction. Unsubstituted (1,1'-(sulfonyldi-4,1-phenylene) bishydrazine is available commercially from Vitas-M, Moscow, Russia (Phone: 7 095 939 5737), and substituted forms can be synthesized from the unsubstituted version. The bis(fluorene-4-carbonyl)alkane compound can be synthesized from 9-fluorenone-4-carbonyl chloride and an alkane diol. Two specific examples are described below in the Examples, and other compounds can be similarly synthesized.

To synthesize the charge transport compositions, the degree of polymerization, i.e., the average value and/or distribution of n, is determined by the concentrations of the reactants, the reaction conditions and the reaction time. In general, the reactants are refluxed for a time from about 2 hours to about 16 hours, although smaller or larger amounts of time can be used. These can be adjusted by a person of ordinary skill in the art, based on the present disclosure, to obtain desired values of the extent of reaction. In general, if a one to one ratio is used of the bis(fluorenone-4-carbonyl) alkane and the bishydrazine, Q is a double bonded oxygen, i.e., O, and Z is two singly bonded hydrogens. A slight excess of bis(fluorenone-4-carbonyl)alkane tends to result in a greater percentage of the Z groups being a bis(fluorenone-4-carbonyl)alkane group. Similarly, a slight excess of the bishydrazine reactant tends to result in a greater percentage of the Q being a sulfonyldiphenylene bishydrazine group.

More specifically, the bis(fluorenone-4-carbonyl)alkane and bishydrazine react to form a bifunctional monomer unit. Under sufficiently dilute reaction conditions and a sufficiently short reaction time, the monomer composition effectively can be formed. To the extent that the reaction proceeds further, a bifunctional monomer unit can further react with other monomer units, bis(fluorenone-4-carbonyl)alkane and/or bishydrazine to form another difunctional compound that can further react. This reaction process continues until the reaction is stopped. The resulting product generally can be characterized by an average molecular weight and a distribution of molecular weights as well as a distribution of identities of substituents Q and Z. Various techniques used for characterizing polymers generally can be used to correspondingly characterize the polymers described herein.

Organophotoreceptor (OPR) Preparation Methods

Following conventional terminology, the number of layers in the OPR refers to the layers with charge transport compositions and/or charge generating compounds. Thus, the presence of overlayers, underlayers, release layers and the like do not alter the single layer versus dual layer terminology.

Positive Inverted Dual Layer OPR

A positive polarity, inverted dual layer organic photoreceptor can be prepared by incorporating a charge transfer compound disclosed herein into the charge transport layer and then over coating this layer with a charge generation solution to form a charge generation layer. The positive inverted dual layer is designed to operate with a positive surface charge that is discharge upon illumination at the point of illumination. An example of a specific approach for forming this structure is presented below.

In one embodiment, a charge transport solution comprising a 1:1 ratio by weight of a charge transfer compound as described herein to a binder, such as polycarbonate Z binder (commercially available from Mitsubishi Gas Chemical under the trade name Lupilon™ Z-200 resin), can be prepared by combining a solution of 1.25 g of one of the charge transfer compounds as described herein in 8.0 g of tetrahydrofuran with 1.25 g of polycarbonate Z in 6.25 g of tetrahydrofuran. The charge transport solution can be hand-coated onto a 76-micrometer (3-mil) thick aluminized polyester substrate (such as a Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 51-micrometer (2-mil) orifice between the blade and polyester, can be used to prepare a film with an 8–10-micron thickness after drying the wet film in an oven at 110° C. for 5–10 min.

A dispersion for forming a charge generation layer can be prepared by micronising 76.1 g of oxytitanium phthalocyanine pigment (H. W. Sands Corp., Jupiter, Fla.), 32.6 g of S-Lec B Bx-5 polyvinylbutryal resin (Sekisui Chemical Co. Ltd.), and 641.3 g of methyl ethyl ketone, using a horizontal sand mill operating in recycle mode for 8 hours. After milling, the charge generation layer base can be diluted with methyl ethyl ketone to decrease the total solids of the solution to 4.0 wt %. The charge generation solution can be hand-coated onto the charge transport layer using a knife coater, set to a 20–25 micron (0.8–1.0 mil) orifice between the blade and charge transfer layer to prepare a sub-micron thick charge generation layer (CGL) film after drying the wet film in an oven at 110° C. for 3–5 min.

Negative Dual Layer OPR

A negative polarity, dual layer organic photoreceptor can be prepared forming a charge generation layer and then incorporating a charge transfer compound disclosed herein into a solution and coating this solution over the charge generation layer to form a charge transfer layer. A negative dual layer is designed to operate with a negative surface charge that is discharged upon illumination at the point of illumination. A specific example for forming a negative dual layer is described below.

In one embodiment, a charge generation layer mill-base dispersion can be prepared by micronising 76.1 g of oxytitanium phthalocyanine pigment, 32.6 g of S-Lec B Bx-5 polyvinylbutryal resin (Sekisui Chemical Co. Ltd.), and 641.3 g of methyl ethyl ketone, using a horizontal sand mill operating in recycle mode for 8 hours. Following milling the charge generating layer base can be diluted with methyl ethyl ketone to decrease the total solids of the solution to 4.0 wt %. The charge generation solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 20–25 micron (0.8–1.0 mil) orifice between the blade and substrate, can be used to prepare the sub-micron thick charge generating layer film after drying the wet film in an oven at 110° C. for 3–5 min.

A charge transport solution comprising a 1:1 ratio by weight of a charge transfer compound described herein to polycarbonate Z binder is prepared by combining a solution of 1.25 g of the charge transfer compound in 8.0 g of tetrahydrofuran with 1.25 g of polycarbonate Z in 6.25 g of tetrahydrofuran. A knife coater, set to a 51-micrometer (2-mil) orifice between the blade and polyester, can be used to prepare an 8–10-micron thick film after drying the wet film in an oven at 110° C. for 5–10 min.

Single Layer OPR

A single layer organic photoreceptor can be prepared by incorporating a charge transfer compound disclosed herein along with a charge generating composition into a single coating solution and then coating this solution over a suitable substrate. A single layer OPR are designed to operate with a surface charge, which may be positive or negative, that is discharged upon illumination at the point of illumination in which the charge is generated in a layer and transported through that layer.

In practice, single layer OPRs are used predominantly with positive surface charges. In general, through the photoconductive and semiconductive materials of interest, electrons have a significantly lower mobility that holes. With low concentrations of charge generating pigment compounds to limit charge trapping in a single layer structure, the electron-hole pairs can be generated some distance from the surface of the OPR after light is absorbed. However, the electron-hole pairs still tend to be closer to the surface than the substrate, such that the electron has less distance to travel than the hole in a positive single layer OPR. The hole from the electron-hole pair can transport through the remaining portion of the OPR to the underlying substrate. Thus, while electrons may travel some distance to neutralize positive charges at the surface of a positively charged OPR, the electrons would still have significantly larger distance to travel to the substrate in a negative single layer OPR. For single layer embodiments, it can be desirable to include an optional electron transport compound to facilitate the electron transport.

However, the use of a dual layer positive OPR is complicated by the formation of a thin charge generating layer over a charge transport layer due to processing complications of dip coating and solvent selection. Also, the thin charge generating layer can be abraded away in use without a good overcoat layer. Thus, a single layer positive OPR may offer some advantages over a positive dual layer system. Since the formation of negative dual layer OPRs do not have the complications of positive dual layer OPRs and since limited electron mobility hinders operation of negative single layer OPRs, negative single layer OPRs generally are less desirable although they are within the scope of the present disclosure for incorporation of the improved charge transport compositions described herein.

In one embodiment especially for the preparation of a single layer OPR, a charge transport pre-mix solution containing a 1:1 ratio by weight of a charge transport composition disclosed herein to polycarbonate Z binder can be prepared by combining a solution of 1.25 g of the charge transfer compound in 8.0 g of tetrahydrofuran with 1.25 g of polycarbonate Z in 6.25 g of tetrahydrofuran. A charge generating layer mill-base dispersion can be prepared by micronising 76.1 g of oxytitanium phthalocyanine pigment, 32.6 g of polycarbonate Z binder resin, and 641.3 g of tetrahydrofuran, using a horizontal sand mill operating in pass mode for 6–8 passes. An electron transport pre-mix solution containing a 1:1.4 ratio of (4-n-butoxycarbonyl-9-fluorenylidene) malonitrile electron transfer compound to Polycarbonate Z binder can be prepared by combining a solution of 1.25 g of one of the electron transporting material in 8.0 g of tetrahydrofuran with 1.75 g of polycarbonate Z in 9 g of tetrahydrofuran.

The single layer coating solution can be prepared by combining 14 g of the charge transport pre-mix, 4.08 g of the electron transport premix and 1.92 g of the charge generating layer mill-base dispersion. The single layer solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 50–75 micron (2–3 mil) orifice between the blade and substrate, can be used to prepare a single layer film with an 8–10 micron thickness after drying the wet film in an oven at 110° C. for 5–10 min.

The invention will now be described further by way of the following examples.

EXAMPLES

Example 1

Synthesis of Bis(9-fluorenone-4-carboxyl)alkanes

The synthesis of bis(9-fluorenone-4-carboxyl) decane is described, and the characterization of the product is outlined.

1,10-Bis(9-fluorenone-4-carboxyl)decane

9-Fluorenone-4-carbonyl chloride (2.44 g, 10 mmol, Aldrich, Milwaukee, Wis.) and 1,10-decanediol (0.87 g, 5 mmol, Aldrich, Milwaukee, Wis.) in the presence of triethylamine (1.01 g, 10 mmol) were refluxed overnight in tetrahydrofuran (THF) (50 mL). THF was removed in vacuum and the compound was recrystallized using ethyl acetate to give yellow crystals with a yield of 64%.

The crystal product had a melting point of 101–102.1° C. Proton NMR analysis yielded peaks that were interpreted as follows: $^1$H-NMR in $CDCl_3$ (300 MHz) chemical shifts (ppm): 1.34–1.46 (m, 12H), 1.81 (quin, J=7.2 Hz, 4H), 4.41 (t, 8.4 Hz, 4H), 7.32–7.37 (m, 4H), 7.50 (td, J=7.8 Hz, 2H),7.70 (d, J=7.2 Hz, 2H), 7.82 (dd, J=1.2 Hz, 7.5 Hz, 2H), 7.93 (dd, J=0.9 Hz, 7.8 Hz, 2H), 8.28 (d, J=7.8 Hz, 2H). Carbon 13 NMR analysis of the product yielded peaks as follows: $^{13}$C-NMR in $CDCl_3$ (75 MHz) chemical shifts (ppm): 26.14, 28.6, 29.2, 29.4, 65.8, 124.1, 126.2, 127.1, 127.3, 128.6, 129.8, 134.4, 135.1, 135.6, 136.0, 143.2, 144.0, 166.8, 193.0.

1,8-Bis(9-fluorenone-4-carboxyl)octane can be prepared similarly by the above procedure for 1,10-Bis(9-fluorenone-4-carboxyl)decane except that 1,8-octanediol (0.732 g, 5 mmole, commercially available from Aldrich, Milwaukee, Wis.) is used instead of 1,10-decanediol. Other bis(9-fluorenone-4-carboxyl) alkanes can be synthesised from this procedure using the appropriate alkane diol.

Example 2

Synthesis of Charge Transport Compositions

The synthesis and characterization of compound 6 above is described. Modification of the process for the synthesis of compounds 7–11 are also described.

Compound 6

Specified quantities of 1,10-bis(9-fluorenone-4-carboxyl)decane (1.5 g, 2.56 mmol, prepared as described above), 1,1'-(sulfonyldi-4,1-phenylene)bishydrazine (0.711 g, 2.56 mmol, available from Vitas-M, Moscow, Russia; Phone: 7 095 939 5737) and 150 ml tetrahydrofuran (THF) were added to a 250 ml round bottom flask equipped with reflux condenser and mechanical stirrer to form a suspension. The suspension was heated to reflux for 15 hours, and the monomers dissolved completely to a yellow colored solution. The reaction mixture was cooled down to the room temperature then concentrated by evaporation and added to 400 ml hexane and the precipitated oligomer was filtered off. The product was purified from THF/hexane. The product was dried at 50° C. vacuum oven for a period of 5 hours. Obtained 1.75 g of yellow amorphous material which was soluble in THF and dimethylformamide (DMF).

The infrared spectrum of the material yielded peaks that were interpreted as follows: IR (KBr): 3350 (—NH), 2930, 2860 (—$CH_2$—), 1590, 1500 (—C=C—), 1385, 1150, 1105 (—$SO_2$—) $cm^{-1}$. The proton NMR spectrum of the material yielded peaks that were interpreted as follows: $^1$H-NMR (THF-$d_8$): δ=1.2–1.36 (m, —$CH_2$—), 1.36–1.9 (m, —$CH_2$—), 4.37 (t, —$OCH_2$—), 6.9–8.6 (m, ar and —CH—), 10.02 (s, —NH—), 10.81 (s, —$NH_2$). The oligomers were also analyzed by gel permeation chromatography the number average molecular weight and the weight average molecular weight as follows: GPC (Dioxane, polystyrene standard): $M_n$ [g/mol]=4.4×10$^3$; $M_w$ [g/mol]=11.2×10$^3$. The polydispersity was $M_w/M_n$=2.5, which provides information on the distribution of molecular weights.

Compound 7

Compound 7 can be prepared according to the procedure for Example 6 except a slight excess (between 0.001 mole and 0.1 mole) of 1,10-Bis(9-fluorenone-4-carboxyl)decane is used.

Compound 8

Compound 8 can be prepared according to the procedure for Example 6 except a slight excess (between 0.001 mole and 0.1 mole) of 1,1'-(sulfonyldi-4,1-phenylene)bishydrazine is used.

Compound 9

One mole of 1,1'-(sulfonyldi-4,1-phenylene)bishydrazine (commercially available from Vitas-M, Moscow, Russia; Phone: 7 095 939 5737) can be mixed with one mole of 1,8-Bis(9-fluorenone-4-carboxyl)octane in the presence of catalytic amount of concentrated sulfuric acid. The mixture is refluxed for 2–16 hours. The crude product can be obtained upon evaporation of the solvent. The crude product is then recrystalyzed.

Compound 10

Compound 10 can be prepared according to the procedure for Example 9 except a slight excess (between 0.001 mole and 0.1 mole) of 1,8-Bis(9-fluorenone-4-carboxyl)octane is used.

Compound 11

Compound 11 can be prepared according to the procedure for Example 9 except a slight excess (between 0.001 mole and 0.1 mole) of 1,1'-(sulfonyldi-4,1-phenylene) bishydrazine is used.

Example 3

Ionization Potential

This example provides measurements of the ionization potential for charge transport composition 6, synthesized as described in Example 2.

Samples for ionization potential (Ip) measurements were prepared by dissolving the compound in tetrahydrofuran. The solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 μm.

No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", Electrophotography, 28, Nr. 4, p. 364. (1989) by E. Miyamoto, Y. Yamaguchi, and M. Yokoyama, which is hereby incorporated by reference. The samples were illuminated with monochromatic light from a quartz monochromator with a deuterium lamp source. The power of the incident light beam was $2$–$5 \cdot 10^{-8}$ W. The negative voltage of −300 V was supplied to the sample substrate. The counter-electrode with the $4.5 \times 15$ mm$^2$ slit for illumination was placed at 8 mm distance from the sample surface. The counter-electrode was connected to the input of the BK2-16 type electrometer, working in the open impute regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}=f(hv)$ dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", Electrophotography, 28, Nr. 4, p. 364. (1989) by E. Miyamoto, Y. Yamaguchi, and M. Yokoyama; and "Photoemission in Solids", Topics in Applied Physics, 26, 1–103. (1978) by M. Cordona and L. Ley, incorporated herein by reference]. The linear part of this dependence was extrapolated to the hv axis and Ip value was determined as the photon energy at the interception point. The ionization potential measurement has an error of ±0.03 eV.

The ionization potential measured for compound 6 was 5.85 eV.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising:

(a) a charge transport composition comprising molecules having the formula

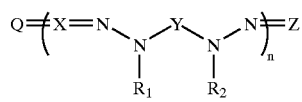

where the average n is between 1 and 1000;

R1 and R2 are, independently, hydrogen, a branched or linear alkyl group, a branched or linear unsaturated hydrocarbon group, an ether group, a cycloalkyl group, or an aryl group;

X is a bis(fluorene-4-carboxyl)alkane group;

Y is a divalent sulfonyldiphenylene group;

Z is X=O where X is double-bonded to the adjacent N or two hydrogens where each hydrogen is independently single-bonded to the adjacent N; and Q is O or N—N(R1)—Y—N(R2)—NH2;

(b) a charge generating compound; and (c) an electrically conductive substrate over which said charge transport composition and said charge generating compound are located.

2. An organophotoreceptor according to claim 1 wherein said organophotoreceptor is in the form of a flexible belt.

3. An organophotoreceptor according to claim 1 wherein said organophotoreceptor is in the form of a drum.

4. An organophotoreceptor according to claim 1 comprising:

(a) a charge transport layer comprising said charge transport composition and a polymeric binder; and (b) a charge generating layer comprising said charge generating compound and a polymeric binder.

5. An organophotoreceptor according to claim 1 wherein said charge transport composition comprises molecules with a formula selected from the group consisting of

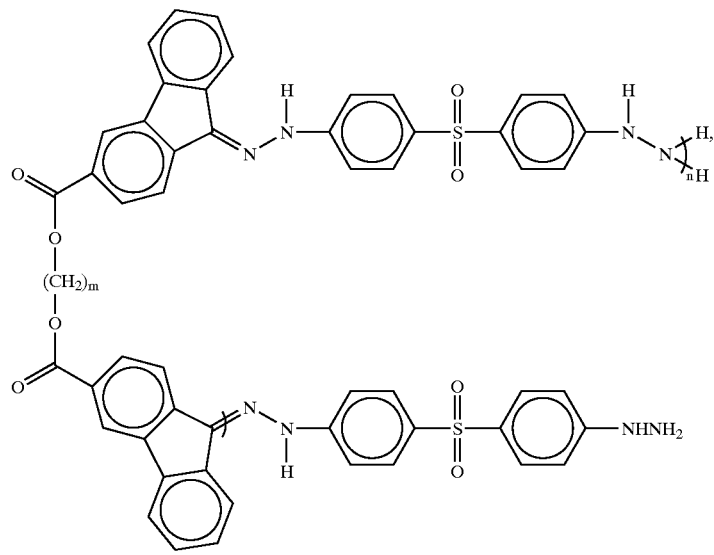

-continued

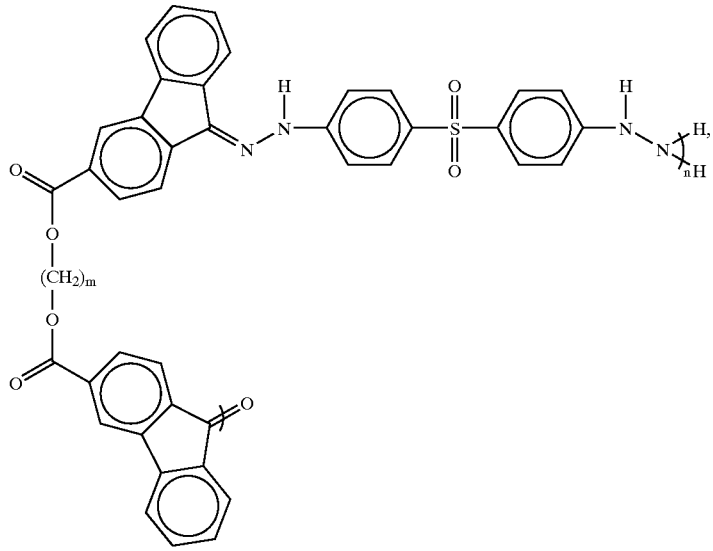

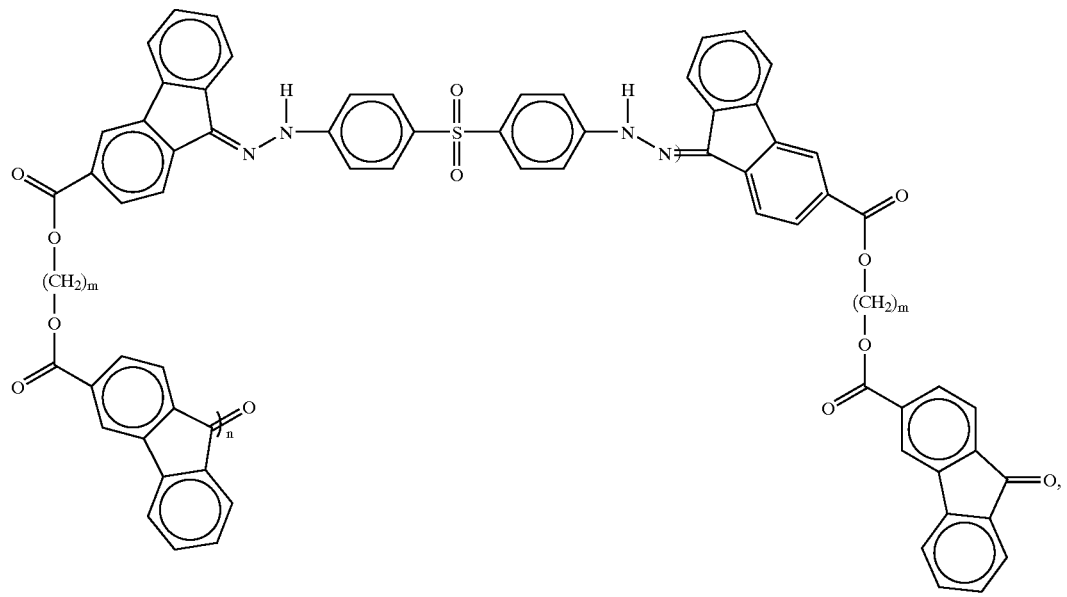

where the average n is between 1 and 1000 and m is between 2 and 30.

6. An organophotoreceptor according to claim 5 wherein m is between 5 and 12.

7. An electrophotographic imaging apparatus comprising:
(a) a plurality of support rollers; and
(b) an organophotoreceptor operably coupled to said support rollers with motion of said support rollers resulting in motion of said organophotoreceptor, said organophotoreceptor comprising:
(i) a charge transport composition comprising molecules having the formula

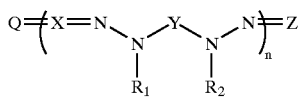

where the average n is between 1 and 1000;

R1 and R2 are, independently, hydrogen, a branched or linear alkyl group, a branched or linear unsaturated hydrocarbon group, an ether group, a cycloalkyl group, or an aryl group;

X is a bis(fluorene-4-carboxyl)alkane group;

Y is a divalent sulfonyldiphenylene group;

Z is X=O where X is double-bonded to the adjacent N or two hydrogens where each hydrogen is independently single-bonded to the adjacent N; and Q is O or N—N(R1)—Y—N(R2)—NH2;

(ii) a charge generating compound; and
(iii) an electrically conductive substrate over which said charge transport composition and said charge generating compound are located.

8. An electrophotographic imaging apparatus according to claim 7 comprising a liquid toner dispenser.

9. A charge transport composition comprising molecules having the formula

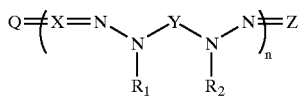

where the avenge n is between 1 and 1000;

R1 and R2 are, independently, hydrogen, a branched or linear alkyl group, a branched or linear unsaturated hydrocarbon group, an ether group, a cycloalkyl group, or an aryl group;

X is a bis(fluorene-4-carboxyl)alkane group;

Y is a divalent sulfonyldiphenylene group;

Z is X=O where X is double-bonded to the adjacent N or two hydrogens where each hydrogen is independently single-bonded to the adjacent N; and Q is O or N—N(R1)—Y—N(R2)—NH2.

10. A charge transport composition according to claim 9 wherein said charge transport composition comprises molecules with a formula selected from the group consisting of

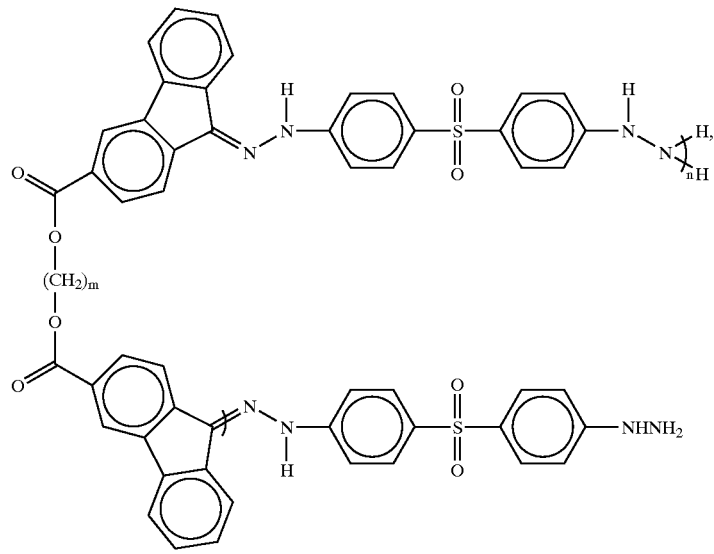

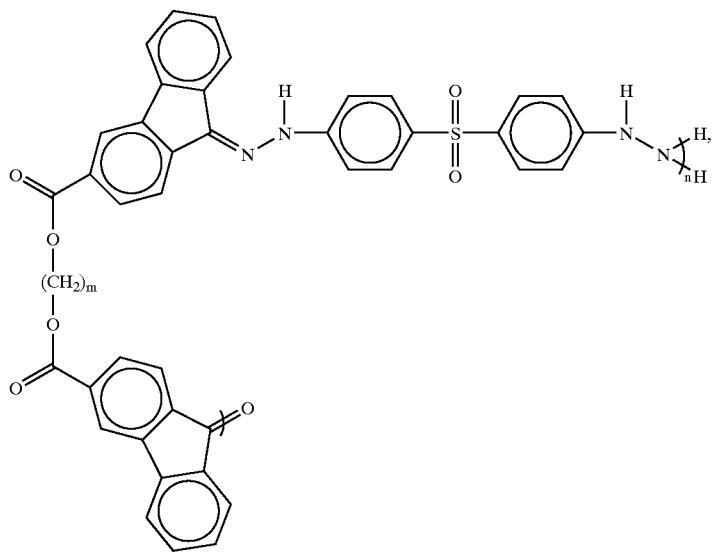

-continued
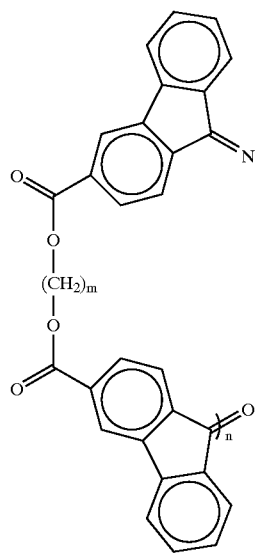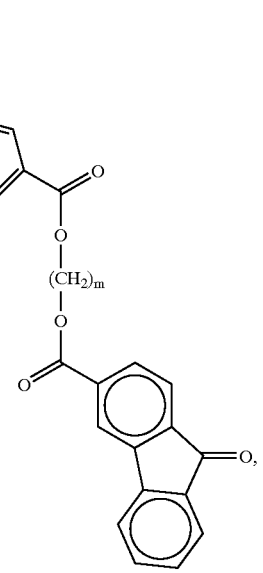
where the average n is between 1 and 1000 and m is between 2 and 30.
11. A charge transport composition according to claim 10 wherein m is between 5 and 12.
12. A charge transport composition according to claim 10 wherein the average n is between 1 and 20.
* * * * *